United States Patent
Kacena et al.

(10) Patent No.: US 10,709,764 B2
(45) Date of Patent: *Jul. 14, 2020

(54) USE OF COMPOUNDS WITH THROMBOPOIETIC ACTIVITY TO PROMOTE BONE GROWTH AND HEALING

(71) Applicant: Osteofuse, Inc., Zionsville, IN (US)

(72) Inventors: Melissa A. Kacena, Zionsville, IN (US); Tien-Min Gabriel Chu, Carmel, IN (US)

(73) Assignee: Osteofuse, Inc., Zionsville, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 16/392,246

(22) Filed: Apr. 23, 2019

(65) Prior Publication Data

US 2019/0240291 A1 Aug. 8, 2019

Related U.S. Application Data

(60) Continuation of application No. 14/978,016, filed on Dec. 22, 2015, now Pat. No. 10,265,381, which is a division of application No. 13/700,904, filed as application No. PCT/US2011/039187 on Jun. 3, 2011, now abandoned.

(60) Provisional application No. 61/351,208, filed on Jun. 3, 2010.

(51) Int. Cl.
| | |
|---|---|
| *A61K 38/19* | (2006.01) |
| *A61K 9/00* | (2006.01) |
| *A61K 45/06* | (2006.01) |
| *C07K 14/52* | (2006.01) |
| *A61L 27/54* | (2006.01) |

(52) U.S. Cl.
CPC .......... *A61K 38/196* (2013.01); *A61K 9/0024* (2013.01); *A61K 45/06* (2013.01); *A61L 27/54* (2013.01); *C07K 14/524* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 6,432,449 | B1 | 8/2002 | Goldenberg |
| 6,511,958 | B1 | 1/2003 | Atkinson |
| 2001/0014662 | A1 | 8/2001 | Rueger |
| 2003/0069401 | A1 | 4/2003 | Oppermann |
| 2008/0031850 | A1 | 2/2008 | Bader |
| 2008/0038236 | A1 | 2/2008 | Gimble |
| 2010/0047214 | A1 | 2/2010 | Abramson |
| 2011/0020299 | A1 | 1/2011 | Bader |
| 2013/0149349 | A1 | 6/2013 | Kacena |

FOREIGN PATENT DOCUMENTS

| | | |
|---|---|---|
| WO | WO-2006071773 A2 | 7/2006 |
| WO | WO-2006088866 A2 | 8/2006 |
| WO | WO-2009121503 A2 | 10/2009 |

OTHER PUBLICATIONS

Wakikawa et al., "Thrombopoietin Inhibits in Vitro Osteoclastogenesis from Murine Bone Marrow Cells", Endocrinology, 138:4160-4166, 1997.
Perry et al., "Mice Rendered Severely Deficient in Megakaryocytes through Targeted Gene Deletion of the Thrombopoietin Receptor c-Mpl Have a Normal Skeletal Phenotype" Calcif. Tissue Int., 81:224-231, 2007.
Kawase et al., J. Tissue Eng. Regen. Med., 3:218-229, 2009.
Ehrenreich et al., PNAS, 102:862-867, 2004.
Samoylenko et al., Cell Signal, 20:154-162, 2008.
Li et al., Br. J. Hematol., 106:345-356, 1999.
Yamada et al., Cell Growth Diff., 9:487-496, 1998.
Broudy et al., Blood, 89:1896-1904, 1997.
Feese et al., PNAS, 101:1816-1821, 2003.
Livnah et al., Science, 283:987-990, 1999.
Hunt et al., Blood, 86:540-547, 1995.
Yuasa et al., J. Clin. Invest., 125:3117-3131, 2015.
Avilucea et al., Adv. Orthop., 709241, 1-7, 2014.
Govender et al., J. Bone Joint Surg. Am., 84-A(12):2123-34, 2002.
Shi et al., Medicine, 96(27): e7413, 2017.
Cahill et al., J. Neurosurg. Spine, 23:86-93, 2015.
Carragee et al., Spine J., 11:471-91, 2011.
Einhorn et al., Nat. Rev. Rheumatol, 11:45-54, 2015.
Mohamad et al., Blood Adv., 1:2520-2528, 2017.
Dorsch, "A Thrombopoietin Receptor Mutant Deficient in Jak-STAT Activation Mediates Proliferation But Not Differentiation in UT-7 Cells", Blood, vol. 94, No. 8, pp. 2676-2685, 1999.
Mowatt et al., "Romiplostim for the treatment of chronic immune or idiopathic thrombocytopenic purpura: a single technology appraisal", Health Technology Assessment, vol. 13, Suppl 2, Article 9, 2009.
Boraiah et al., Complications of Recombinant Human BMP-2 for Treating Complex Tibial Plateau Fractures, Clin. Orthop. Relat. Res., 467:3257-3262, 2009.
Carver-Moore et al., Low Levels of Erythroid and Myeloid Progenitors in Thrombopoietin- and c-mpl-Deficient Mice, Blood, 88(3):803-808, 1996.

(Continued)

*Primary Examiner* — Robert T. Crow
*Assistant Examiner* — John P Nguyen
(74) *Attorney, Agent, or Firm* — Cesari and McKenna, LLP (57) ABSTRACT

A method for treating a defect site in a living bone of an animal by applying an exogenous compound having thrombopoietic activity to the defect site in an amount effective to induce thrombopoiesis. The exogenous compound activates a thrombopoietin receptor, leading to accelerated bone formation at the defect site. Also provided is a method for repairing a segmental bone defect in an animal bone by inserting into the segmental bone defect a biodegradable bone repair scaffold that contains a compound having thrombopoietic activity. The compound activates a thrombopoietin receptor and accelerates bone formation such that bridging occurs at the segmental bone defect.

25 Claims, 8 Drawing Sheets

Specification includes a Sequence Listing.

(56) References Cited

OTHER PUBLICATIONS

Chu et al., Segmental Bone Regeneration Using a Load Bearing Biodegradable Carrier of Bone Morphogenetic Protein-2, Biomaterials, 28(3):459-467, 2007.
Cobos et al., The Cylindrical Titanium Mesh Cage for Treatment of a Long Bone Segmental Defect: Description of a New Technique and Report of Two Cases, Journal of Orthopaedic Trauma, 2000, 14(1):54-59.
Dominici et al., Restoration and Reversible Expansion of the Osteoblastic Hematopoietic Stem Cell Niche After Marrow Radioablation, Blood, 2009, 114:2333-2343.
Frey et al., Adenovirus Long-Term Expression of Thrombopoietin In Vivo: A New Model for Myeloproliferative Syndrome and Osteomyelofibrosis, Schweiz. Med. Wochenschr., 1998,128(42):1587-1592 [English Language Abstract Only].
Frey et al., Adenovector-Mediated Expression of Human Thrombopoietin cDNA in Immune-Compromised Mice: Insights into the Pathophysiology of Osteomyelofibrosis, The Journal of Immunology, 1998, 160:691-699.
Goldstein, Tissue Engineering Solutions for Traumatic Bone Loss, Journal of the American Academy of Orthopaedic Surgeons, 2006, 14:S152-S156.
Green et al., Management of Segmental Defects by the Ilizarov Intercalary Bone Transport Method, Clinical Orthopaedics & Related Research, 1992, 280:136-142.
Green et al., Skeletal Defects A Comparison of Bone Grafting and Bone Transport for Segmental Skeletal Defects, Clinical OrthopAedics & Related Research, 1994, 301:111-117.
Johnson et al., Repair of Segmental Defects of the Tibia With Cancellous Bone Grafts Augmented With Human Bone Morphogenetic Protein: A Preliminary Report, Clinical Orthopaedics & Related Research, 1988, 236:249-257.
Kacena et al., Megakaryocyte-Osteoblast Interaction Revealed in Mice Deficient in Transcription Factors GATA-1 and NF-E2, Journal of Bone and Mineral Research, 2004, 19(4):652-660.
Kacena et al., Loss of the Transcription Factor p45 NF-E2 Results in a Developmental Arrest of Megakaryocyte Differentiation and the Onset of a High Bone Mass Phenotype, Bone, 2005, 36(2):215-223.
Karaoglu et al., Experimental Repair of Segmental Bone Defects in Rabbits by Demineralized Allograft Covered by Free Autogenous Periosteum, Injury, 2002, 33(8):679-683.
Kuter et al., Efficacy of Romiplostim in Patients With Chronic Immune Thrombocytopenic Purpura: A Double-Blind Randomised Controlled Trial, Lancet, 2008, 371:395-403.
Lane et al., Biosynthetic Bone Grafting, Clinical Orthopaedics & Related Research, 1999, 367S:S107-S117.
Lieberman et al., Current Concepts Review—The Role of Growth Factors in the Repair of Bone, Journal of Bone & Joint Surgery, 2002, 84-A(6):1032-1044.
Salkeld et al., The Effect of Osteogenic Protein-1 on the Healing of Segmental Bone Defects Treated With Autograft Dr Allograft Bone, Journal of Bone & Joint Surgery, 2001, 83-A(6):803-816.
Shivdasani et al., Transcription Factor NF-E2 is Required for Platelet Formation Independent of the Actions of Thrombopoietin/MGDF in Megakaryocyte Development, Cell, 1995, 81:695-704.
Shivdasani et al., A Lineage-Selective Knockout Establishes the Critical Role of Transcription Factor GATA-1 in Megakaryocyte Growth and Platelet Development, The EMBO Journal, 1997, 16(13):3965-3973.
Suva et al., Platelet Dysfunction and a High Bone Mass Phenotype in a Murine Model of Platelet-Type von Willebrand Disease, The American Journal of Pathology, 2008, 172(2):430-439.
Taylor et al., SU104: A Novel Role for Thrombopoietin in Regulating Osteoclast Development, ASBMR 30th Annual Meeting, JBMR, 2008, 23:S268.
Villeval et al., High Thrombopoietin Production by Hematopoietic Cells Induces a Fatal Myeloproliferative Syndrome in Mice, Blood, 1997, 90(11):4369-4383.
Watson et al., Management Strategies for Bone Loss in Tibial Shaft Fractures, Clinical Orthopaedics & Related Research, 1995, 315:138-152.
Weinberg et al., Early Fibular Bypass Procedures (Tibiofibular Synostosis) for Massive Bone Loss in War Injuries, Journal of Trauma, 1979, 19(3):177-181.
Yan et al., A Model of Myelofibrosis and Osteosclerosis in Mice Induced by Overexpressing Thrombopoietin (mpl_Ligand): Reversal of Disease by Bone Marrow Transplantation, Blood, 1996, 88(2):402-409.
Yan et al., Chronic Exposure to Retroviral Vector Encoded MGDF (mpl-Ligand) Induces Lineage-Specific Growth and Differentiation of Megakaryocytes in Mice, Blood, 1995, 86(11):4025-4033.
PCT International Search Report, PCT/US2011/039187, dated Feb. 28, 2012.
PCT International Preliminary Report on Patentability, PCT/US2011/039187, dated Dec. 4, 2012.

SEQUENCE LISTING

```
<160> NUMBER OF SEQ ID NOS: 3

<210> SEQ ID NO 1
<211> LENGTH: 174
<212> TYPE: PRT
<213> ORGANISM: Mus musculus

<400> SEQUENCE: 1

Ser Pro Val Ala Pro Ala Cys Asp Pro Arg Leu Leu Asn Lys Leu Leu
1               5                   10                  15

Arg Asp Ser His Leu Leu His Ser Arg Leu Ser Gln Cys Pro Asp Val
                20                  25                  30

Asp Pro Leu Ser Ile Pro Val Leu Leu Pro Ala Val Asp Phe Ser Leu
            35                  40                  45

Gly Glu Trp Lys Thr Gln Thr Glu Gln Ser Lys Ala Gln Asp Ile Leu
50                  55                  60

Gly Ala Val Ser Leu Leu Leu Glu Gly Val Met Ala Ala Arg Gly Gln
65                  70                  75                  80

Leu Glu Pro Ser Cys Leu Ser Ser Leu Leu Gly Gln Leu Ser Gly Gln
                85                  90                  95

Val Arg Leu Leu Leu Gly Ala Leu Gln Gly Leu Leu Gly Thr Gln Leu
                100                 105                 110

Pro Leu Gln Gly Arg Thr Thr Ala His Lys Asp Pro Asn Ala Leu Phe
```

```
              115                 120                 125
Leu Ser Leu Gln Gln Leu Leu Arg Gly Lys Val Arg Phe Leu Leu Leu
        130                 135                 140

Val Glu Gly Pro Thr Leu Cys Val Arg Arg Thr Leu Pro Thr Thr Ala
145                 150                 155                 160

Val Pro Ser Ser Thr Ser Gln Leu Leu Thr Leu Asn Lys Phe
                165                 170
```

<210> SEQ ID NO 2
<211> LENGTH: 174
<212> TYPE: PRT
<213> ORGANISM: Homo sapiens

<400> SEQUENCE: 2

```
Ser Pro Ala Pro Pro Ala Cys Asp Leu Arg Val Leu Ser Lys Leu Leu
1               5                   10                  15

Arg Asp Ser His Val Leu His Ser Arg Leu Ser Gln Cys Pro Glu Val
            20                  25                  30

His Pro Leu Pro Thr Pro Val Leu Leu Pro Ala Val Asp Phe Ser Leu
        35                  40                  45

Gly Glu Trp Lys Thr Gln Met Glu Glu Thr Lys Ala Gln Asp Ile Leu
    50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
    130                 135                 140

Val Gly Gly Ser Thr Leu Cys Val Arg Arg Ala Pro Pro Thr Thr Ala
145                 150                 155                 160

Val Pro Ser Arg Thr Ser Leu Val Leu Thr Leu Asn Glu Leu
                165                 170
```

<210> SEQ ID NO 3
<211> LENGTH: 174
<212> TYPE: PRT
<213> ORGANISM: Rattus rattus

<400> SEQUENCE: 3

```
Ser Pro Val Pro Pro Ala Cys Asp Pro Arg Leu Leu Asn Lys Leu Leu
1               5                   10                  15

Arg Asp Ser Tyr Leu Leu His Ser Arg Leu Ser Gln Cys Pro Asp Val
            20                  25                  30

Asn Pro Leu Ser Ile Pro Val Leu Leu Pro Ala Val Asp Phe Ser Leu
        35                  40                  45

Gly Glu Trp Lys Thr Gln Thr Glu Gln Ser Lys Ala Gln Asp Ile Leu
    50                  55                  60

Gly Ala Val Ser Leu Leu Leu Glu Gly Val Met Ala Ala Arg Gly Gln
65                  70                  75                  80

Leu Glu Pro Ser Cys Leu Ser Ser Leu Leu Gly Gln Leu Ser Gly Gln
                85                  90                  95

Val Arg Leu Leu Leu Gly Ala Leu Gln Gly Leu Leu Gly Thr Gln Leu
```

```
                100                 105                 110
Pro Pro Gln Gly Arg Thr Thr Ala His Lys Asp Pro Ser Ala Leu Phe
        115                 120                 125

Leu Ser Leu Gln Gln Leu Leu Arg Gly Lys Val Arg Phe Leu Leu Leu
    130                 135                 140

Val Glu Gly Pro Ala Leu Cys Val Arg Arg Thr Leu Pro Thr Thr Ala
145                 150                 155                 160

Val Pro Ser Arg Thr Ser Gln Leu Leu Thr Leu Asn Lys Phe
            165                 170
```

USE OF COMPOUNDS WITH THROMBOPOIETIC ACTIVITY TO PROMOTE BONE GROWTH AND HEALING

CROSS-REFERENCE TO RELATED APPLICATIONS

This application is a continuation of U.S. patent application Ser. No. 14/978,016 filed on Dec. 22, 2015, now U.S. Pat. No. 10,265,381, which is a divisional of U.S. patent application Ser. No. 13/700,904 filed on Feb. 27, 2013, now abandoned, which is the national stage of International Application No. PCT/US2011/039187 filed on Jun. 3, 2011, which claims the benefit of U.S. Provisional Application No. 61/351,208 filed on Jun. 3, 2010. The content of the prior applications is incorporated herein by reference in its entirety.

FIELD OF THE INVENTION

Aspects of the invention relate to promoting bone growth in mammals by treating bone defects, especially breaks and/or gaps with compounds that exhibit thrombopoietic activity.

BACKGROUND

Each year, approximately 6 million fractures occur in the United States. These fractures result in over 9 million physician visits and a loss of more than 36 million work days [1]. Fractures resulting in segmental defects of the long bones are particularly difficult to manage, often requiring multiple surgeries in an attempt to achieve adequate union and function [2].

There are many causes of segmental defects. They may be the result of many causes, including tumor resection, treatment of infection, failure of arthroplasty—but the most common cause is from trauma, particularly motor vehicle associated trauma. High energy, open fractures may result in direct immediate bone loss or may require debridement of devascularized contaminated bone. This is a common, yet challenging, problem for orthopaedic traumatologists and their patients. The incidence of severe lower extremity trauma in civilian life is certainly increasing due to the epidemic of road traffic accidents around the world. In the US alone, over a quarter million admissions annually are due to lower extremity injuries, and it is estimated that more than half are the result of high energy mechanisms [3].

The recent military conflicts around the world have also increased the need to address high energy or blast injuries which often involve bone trauma and tissue loss. Over 75% of modern war injuries involve the extremities, predominantly caused by fragments from explosive devices, which commonly cause open fractures with contaminated wounds and tissue loss [4]. These examples illustrate that there are needs in many areas of orthopaedics to improve bone healing.

Achieving bone union can be difficult in all aspects of orthopaedics, including spine, trauma, and upper extremity surgery. Failure to achieve bone union results in multiple additional surgeries, significant morbidity, and ultimately can lead to loss of extremity function or amputation for the patient. In cases of fracture nonunion alone, some 450,000 grafting procedures are performed yearly [5]. Many additional bone grafting procedures are required for spinal fusion. The gold standard for grafting to achieve bone union/fusion is the use of donor bone (called autograft) from the patient's hip. This often leaves a patient with a very painful donor site, which may not resolve. There is a need then for biologic enhancements for bone healing that do not require the harvesting of a patient's iliac crest hip bone trauma or tumour. Some aspects of the invention address this need.

SUMMARY

Some embodiments of the invention include methods for treating bone comprising the steps of: administering a compound that exhibits thrombopoietic activity in order to promote the healing of a defect, disease or injury in at least one bone. In some embodiments, the compound having thrombopoietic activity is selected from the group consisting of thrombopoietin (TPO). including recombinant forms of TPO, compounds such as romiplostim and megakaryocyte growth and development factor (MGDF). In some embodiments, at least one compound exhibiting thrombopoietic activity is administered, along with at least one other compound that stimulates bone growth such as BMP-2. In some embodiments, the compounds are administered along with at least one additional compound such as an antibiotic, bone filler, glue, or the like.

Levels of compounds that exhibit thrombopoietic activity such as recombinant TPO that are required or desirable for promoting bone growth and healing will vary from patient to patient depending on factors such as the size of the patient, age, gender, general health and the type and extent of the disease, defect or injury being treated. In mice, an amount of recombinant TPO on the order of about 1.0 µg is sufficient to promote bone healing while about 10 µg of recombinant TPO exhibited better results in rats. Determining the correct dosage for patients, including human patients, required for effective treatment is well within the skill of those of ordinary skill in the medical arts and certainly will not require undue experimentation.

In some embodiments, methods that include contacting bone with an exogenous source of a compound exhibiting thrombopoietic activity occurs either in vivo or in vitro. In some embodiments of the invention, compounds having thrombopoietic activity are administered at the same time that a bone defect, disease or injury is being treated and the compound is not placed in direct contact with the bone.

In some embodiments, the compound exhibiting thrombopoietic activity is included in at least one formulation selected from the group consisting of; a paste, a glue, a coating, a gel, a powder and a liquid.

Some embodiments of the invention include devices for treating bone defects, comprising: at least one physical support and at least one first compound that exhibits thrombopoietic activity. In some of these embodiments, the device is biodegradable and in some embodiments, the device is the form of a scaffold that can be used to stabilize, hold fast or support a bone. In some embodiments, the compounds that exhibits thrombopoietic activity is recombinant TPO and/or romiplostim and/or a romiplostim like molecule and/or megakaryocyte growth and development factor (MGDF) and/or a compound that acts like MGDF. In some embodiments, the compounds exhibiting thrombopoietic activity can be injected directly or, at least, near to a bone or to a portion of a bone being treated. In some embodiments, the carrier for the compound exhibiting thrombopoietic activity formulated for use in bone healing is in the form of a gel, suspension, paste, glue, powder and the like. It may also be administered as a patch, disc, or implant. It may also be applied to the surface of an object that comes into direct or indirect contact with at least a portion of a bone. Such objects include, but are not limited to, screws, pegs, posts, staples, nails, wires, springs, braces levers and the like. Formulations and objects that include compounds having exhibiting thrombopoietic activity may also be used to promote bone growth and/or healing in dental applications.

Some embodiments of the invention include methods for treating bone defects, diseases, or injuries, comprising the steps of: identifying a bone defect; providing a biodegradable device, wherein said device includes at least one compound that exhibits thrombopoietic activity; and contacting said biodegradable device with the bone defect. In some embodiments, the device is biodegradable; for example, a biodegradable scaffold. In some embodiments, the treated bone is a mammalian bone; for example, a human, mouse or rat bone. In some embodiments, the device further includes at least means for anchoring the device such as a pin, screw, staple, brace, clamp or the like.

Some aspects of the invention include devices for treating bone defects, comprising: at least one physical support and at least one source of TPO. In some embodiments, the scaffolding is biodegradable. In some embodiments, a compound having thrombopoietic activity is directly placed near or in contact with a portion of bone or near a portion of bone. Methods for directly delivering compound having thrombopoietic activity in vivo include injections and/or surgical interventions.

Still other embodiments include methods of treating a bone defect, comprising the steps of: identifying a bone defect; providing a biodegradable device, wherein said device includes TPO; and contacting said biodegradable device with the bone defect. In some embodiments, the scaffolding is biodegradable. In some embodiments, the bone defect is in a human or animal patient. In some embodiments, the scaffolding may include at least one additional bioactive compound such as an additional growth factor and/or a compound that inhibits infection. In some embodiments, the scaffolding includes at least one device or feature to attaching the scaffolding to patient's bone.

SEQUENCE LISTING

SEQ. ID NO. 1. Recombinant mouse thrombopoietin (TPO).
SEQ. ID NO. 2 Recombinant human thrombopoietin (TPO).
SEQ. ID NO. 3 Recombinant rat thrombopoietin (TPO).

DESCRIPTION

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates are within the scope of the claimed invention.

Despite advances in surgical technique and implants, orthopaedic surgeons are still challenged to obtain fracture union, spine fusion, or bridging of segmental defects. The gold standard for grafting to achieve bone union/fusion is the use of donor bone (autograft) from the patient's hip. Even autografting is sometimes not sufficient to achieve healing, exacerbated by the fact that the harvest of bone from a patient's hip often leaves a patient with a very painful donor site, which may not resolve. For this reason, orthopaedic surgeons desire a biologic enhancement for bone healing that does not require the harvesting of a patient's iliac crest hip bone. Other than autograft, bone morphogenetic proteins (BMPs) are currently the only other biologic option shown to be capable of bridging critical sized bone defects. Although BMP's are potent in promoting bone regeneration, they can lead to heterotopic bone formation which may require additional surgery, and they are also expensive. Therefore, researchers are constantly seeking new candidate molecules that can provide equivalent or better treatment results.

In order to overcome the limitations in current orthopaedic practice, researchers are exploring tissue engineering. One approach involves combining biodegradable scaffolds with bone growth inducing factors such as bone morphogenetic proteins (BMP) and demineralized bone matrix. Using this technique some missing bone tissue in segmental defects or nonunions can be healed. BMP-2 is a potent stimulator of bone regeneration. Unfortunately, the use of BMP-2 may lead to heterotopic bone formation that may require additional surgery. Still another downside to using BMP-2 is it's expensive. Due to the relatively high cost of BMP and inconsistent results from demineralized bone matrix, researchers are constantly seeking new molecules and methods that can provide equivalent or better treatment results than the existing treatment for segmented bone loss. Although a number of growth factors (TGF-β, FGF, IGF, PDGF) have been shown to promote bone healing, prior to this work none, other than BMP's, have been shown to be capable of healing a critical sized defect. Data disclosed herein demonstrates that not only can thrombopoietin (TPO, the main megakaryocyte growth factor) heal a critical sized defect, but it appears to do so more robustly than does BMP-2. As detailed below, the trabeculae are thicker and the callus appears to have undergone more extensive remodeling and/or less heterotopic bone formation in defects treated with TPO than bone defects treated with BMP-2.

To overcome the disadvantages of donor site morbidity while maintaining the biologic attractiveness of autograft, tissue engineering is now being explored. The tissue engineering approach uses a biodegradable scaffold which can deliver the biological factors and/or cells to the defect site and can provide a temporal attachment for the forming of new tissues. After the new tissue forms, the carrier will degrade and be resorbed by tissue, leaving no artifact behind. Current options available to treat segmental defects include autologous bone graft, allograft, and distraction osteogenesis. Each option is associated with possible significant morbidity. To overcome these limitations, tissue engineering has been a major focus of recent research. Currently, FDA approved growth factors shown to improve healing in segmental defects are BMP-2 and 7. However, BMPs also have significant limitations, such as cost and method of delivery in a segmental defect.

Recently, a high strength biodegradable scaffold used it to carry bone morphogenetic protein-2 (BMP-2) was reported. In this report a rat femur model was used to demonstrate significant bone formation in experimental groups. The results showed that the scaffold is sufficient to sustain load in the segmental defect and also can successfully release BMP-2 to facilitate healing [19].

Unfortunately, the use of BMP-2 in humans can be cost-prohibitive. Due to the relative high cost of BMP, researchers are constantly seeking new candidate molecules that can provide equivalent or better treatment results in place of BMP or demineralized bone matrix.

It has also been demonstrated that megakaryocytes (MKs) enhance osteoblast proliferation by 3- to 6-fold and increase bone formation in vivo [18, 20]. As reported herein, coating scaffolds that include megakaryocyte growth factor, such as TPO, enhance bone regeneration.

It appears that with TPO-coated scaffolds more extensive remodeling and/or less heterotopic bone formation has occurred than that observed with BMP-2. Importantly, these studies demonstrate that osteoclast progenitors express the TPO receptor and that treatment of these cells with TPO increases osteoclastogenesis by up to 5-fold [4]. These results show that the here-to-fore previously unrecognized role of TPO in osteoclastogenesis is critically important in the enhanced bone healing seen with TPO coated scaffolds as it appears to lead to accelerate coupling/remodeling and therefore accelerated bone healing.

Studies demonstrate that 1) Mice with increased numbers of bone marrow-derived MKs have up to a 300% increase in bone volume; and 2) MKs enhance OB proliferation up to 6-fold in vitro and 2-3 fold in vivo. Additional data demonstrates that OC progenitors express the TPO receptor, c-mpl, and that stimulation of OC progenitors with TPO results in an increase in mature OC formation in vitro (up to 5-fold). [4].

Mouse models where transcription factors that are thought to be necessary for normal MK differentiation were either markedly reduced or knocked-out, GATA-1 and NF-E2, respectively, are known. As shown in FIG. 1, these mice develop a marked increase in bone marrow MK number with a concomitant reduction in platelet number and a dramatic increase in trabecular bone [1, 29, 30]. Of interest, mice that overexpress TPO also have a 4-fold increase in bone marrow MK number and develop an osteosclerotic bone phenotype with increased bone mineral density [31-35]. Thus, there are currently 3 known mouse models with increased bone marrow megakaryopoiesis, which results in significant increases in bone volume due to increases in bone formation.

Notably, a novel mouse model of platelet-type von Willenbrand disease (Pt-vWD), with a platelet phenotype identical to the human form of the disease, showed a marked increase in splenic MK with splenomegaly and a high bone mass phenotype with decreased serum measures of bone resorption [36]. In comparison, the TPO overexpressing mice and the transcription factor deficient mice (GATA-1 and NF-E2) show a significantly elevated number of bone marrow and splenic MKs. Data from Suva et al. [36] suggest that increases in splenic MK number results in a marked decrease in bone resorption which in turn results in a high bone mass phenotype. Conversely, when bone marrow MK number is elevated, anabolic bone formation is increased, which also leads to a high bone mass phenotype [1, 29, 30]. Therefore, these mouse models suggest that in order for anabolic bone formation to occur, MKs must be present in the bone marrow where they can be in direct contact with OBs.

Figure 1A:
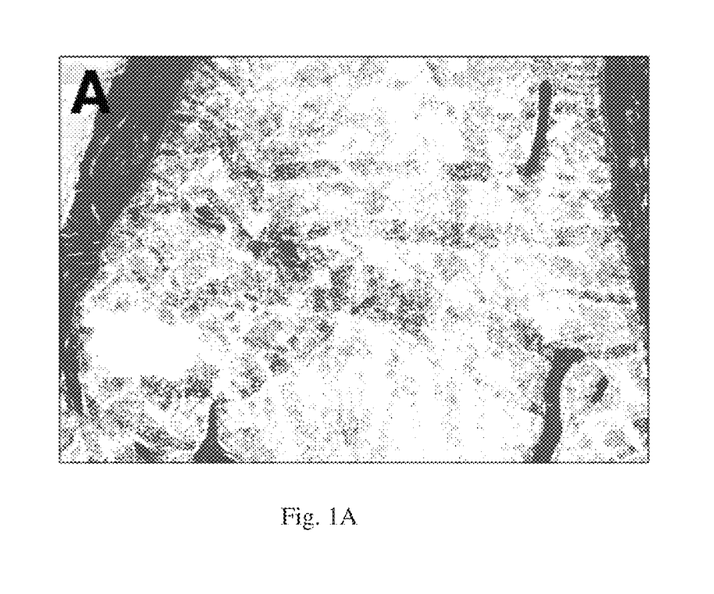
FIG. 1A. Histological assessment of C57BL/6 long bones. Toluidine blue stained proximal tibiae from 9-month-old C57BL/6 control mice. C57BL/6 tibiae show the typical trabecular and cortical bone volume just above the growth plate and otherwise unremarkable histology seen in older mice (50× original magnification).
Figure 1B:
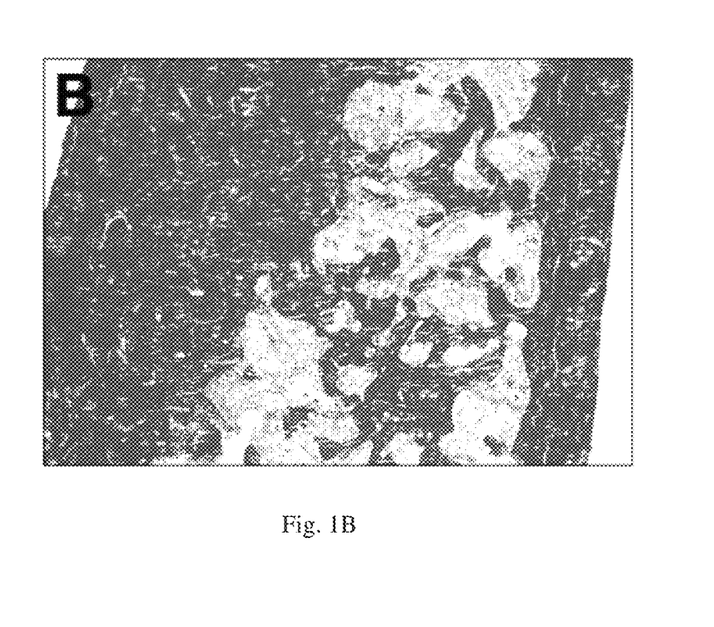
FIG. 1B. Toluidine blue stained proximal tibiae from 9-month-old GATA-1 deficient mice. GATA-1 deficient tibiae illustrate the striking increase in trabecular and cortical bone (50× original magnification).
Figure 1C:
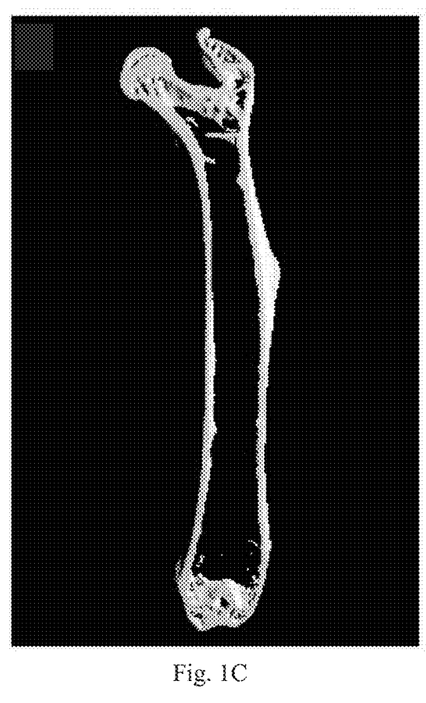
FIG. 1C. µCT analysis of femurs from. 5-month-old C57BL/6 mice. C57BL/6 femurs are normal in appearance with respect to the medullary canal, secondary spongiosa, and mid-diaphyseal cortical bone.
Figure 1D:
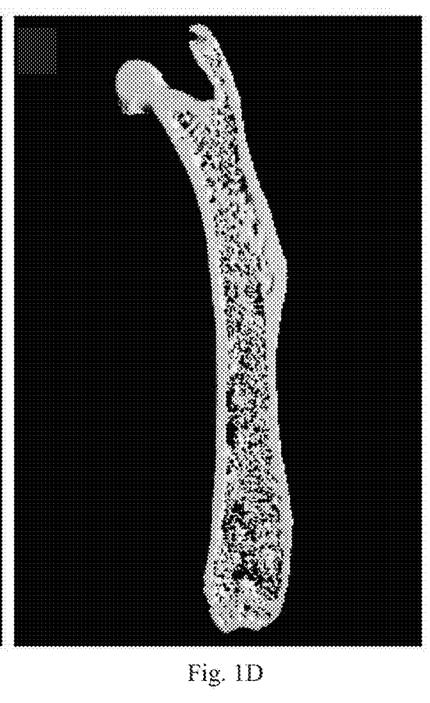
FIG. 1D. µCT analysis of femurs from 5-month-old GATA-1 deficient mice. GATA-1 deficient femurs show cortical thickening, increased trabecular bone volume in the entire medullary canal, including bone filling the proximal metaphysis and part of the diaphyseal shaft.
Figure 2:
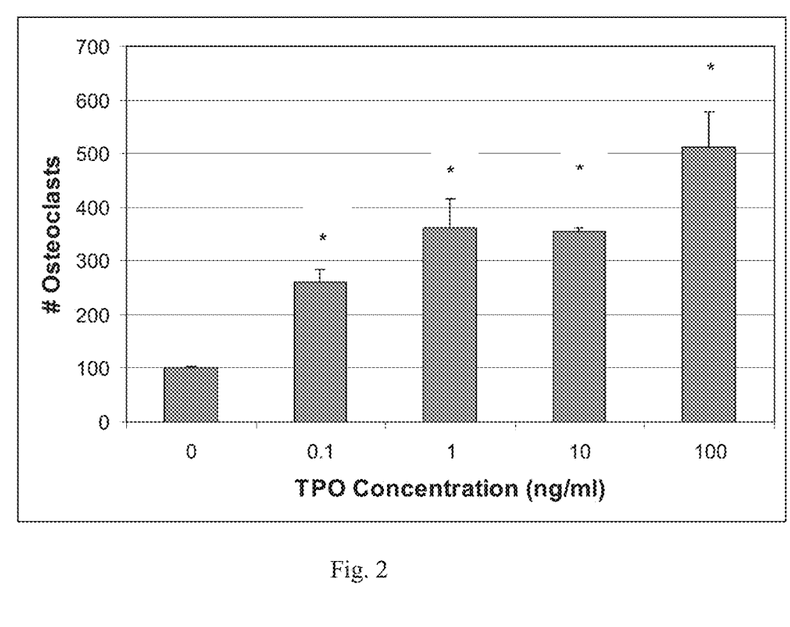
FIG. 2. Bar graph showing C57BL/6 bone marrow macrophages (BMMs) were cultured with M-CSF (30 ng/ml) and RANKL (50 ng/ml). While culturing C57BL/6 BMMs with M-CSF and RANKL (no TPO) results in the generation of mature TRAP$^+$ multinucleated osteoclasts (OCs) (>3 nuclei), culturing these cells with TPO (0.1-100 ng/ml) enhances the number OCs by >2-fold. *$p<0.05$ FIG. 3A. Representative micrograph of cultures of BMMs stimulated with M-CSF (30 ng/ml) and RANKL (50 ng/ml). TRAP staining shows mature, multinucleated OCs developed in the absence of TPO.
Figure 3A:
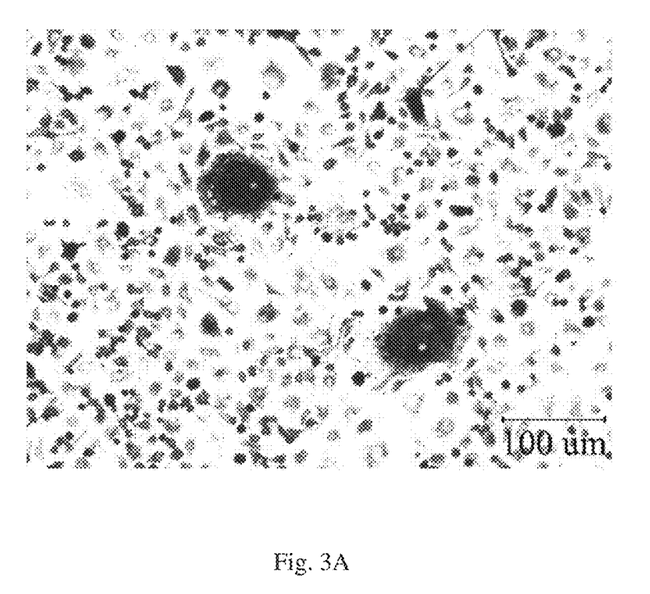
Figure 3B:
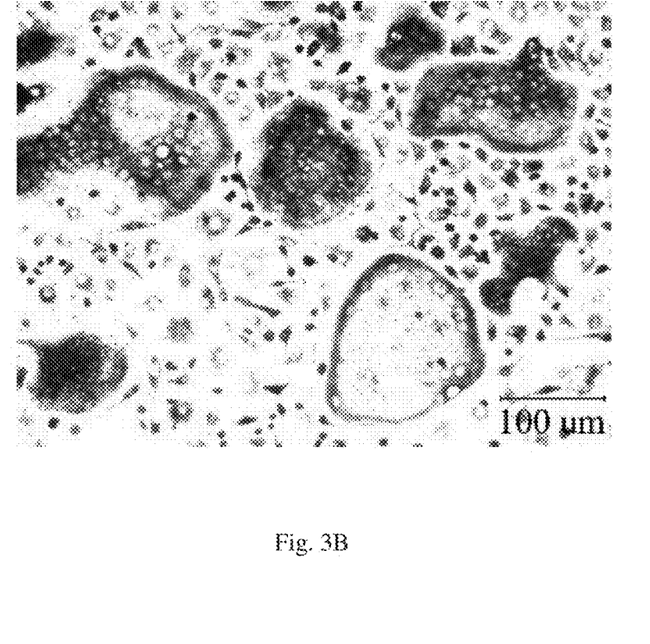
FIG. 3B. Representative micrograph of cultures of BMMs stimulated with M-CSF (30 ng/ml) and RANKL (50 ng/ml). TRAP staining shows mature, multinucleated OCs developed in the presence of TPO (100 ng/ml). Significantly more OCs developed with TPO stimulation.

It should be noted that Perry et. al. (2007) recently examined the c-mpl deficient mice predicting that due to the ~90% reduction in bone marrow MKs that bone volume would be reduced compared to control mice, where in fact they reported no difference [37]. We are in the process of confirming these data and extending them with careful analysis of OB number and bone formation as well as OC assessment. But, in understanding the bone mass in these mice, it is important to note that these mice have been documented as having a significant reduction in myeloid lineage cells [38], possibly owing to the importance of c-mpl on hematopoietic stem cells as well as our novel observation regarding c-mpl expression on OC progenitors [4]. With regard to c-mpl expression on OCs, we found that OC progenitors express c-mpl (mRNA expression by real-time PCR as well as protein expression by Western blot and immunohistochemistry) and that stimulation of osteoclast progenitors results in up to a 5-fold increase in formation of mature OCs in vitro. FIGS. 2 and 3 illustrate these data. Therefore, the bone volume observed in c-mpl deficient mice may be similar to control levels due to a reduction in bone turnover as well as a reduction in formation.

Figure 4A:
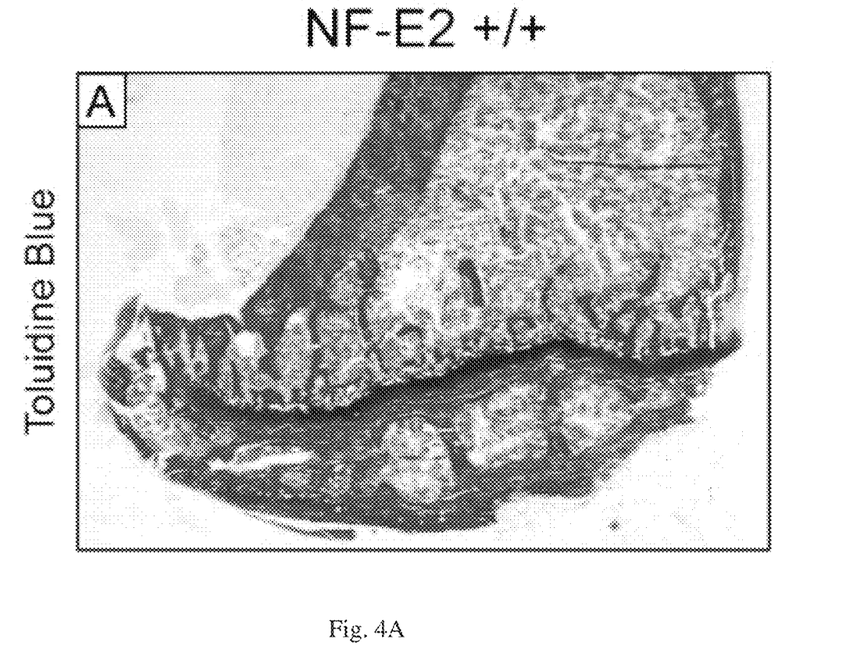
FIG. 4A. 129/Sv (control mice) spleen cells were transferred into irradiated 129/Sv-recipient mice. Toluidine blue staining of tibiae, 8 weeks following adoptive transfer shows bones similar to 129/Sv control mice.
Figure 4B:
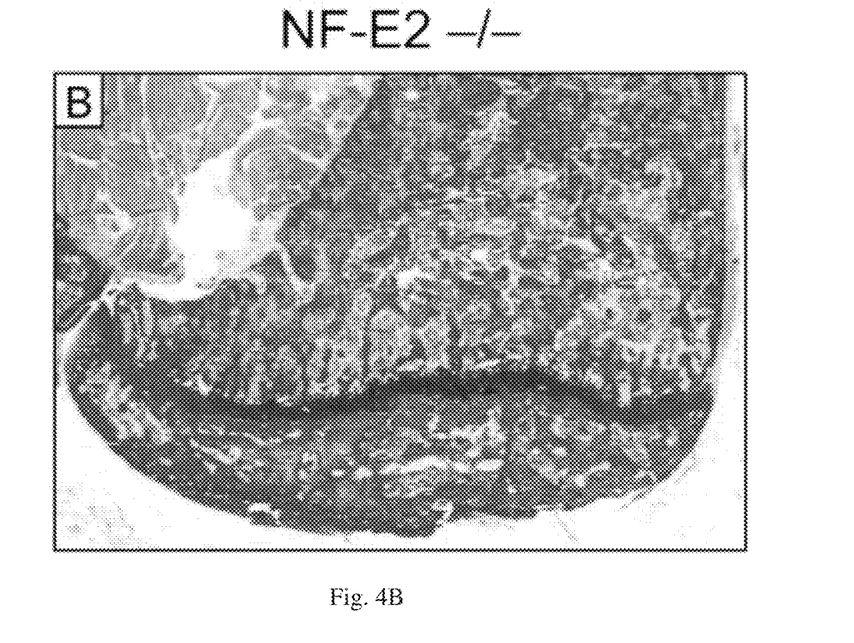
FIG. 4B. NF-E2$^{-/-}$ spleen cells were transferred into irradiated 129/Sv-recipient mice. The NF-E2$^{-/-}$ bone phenotype was successfully transferred. Histomorphometric measurements showed that trabecular bone volume was similar to that seen in NF-E2$^{-/-}$ mice.

Additional evidence for the stimulation of OB proliferation and bone formation by MKs comes from in vivo adoptive transfer and irradiation studies. To better understand the mechanism of increased bone formation in NF-E2$^{-/-}$ mice, we adoptively transferred the MK/bone phenotype into lethally irradiated 129/Sv-recipient mice using spleen cells [2]. Because the marrow cavity as filled with bone, spleen cells rather than bone marrow cells were used for the adoptive transfer. Spleen cells are an excellent source of immature MKs (up to 5 fold-increase) and hematopoietic progenitor cells due to the extra-medullary hematopoiesis. Transfer of the NF-E2$^{-/-}$ phenotype to recipient mice was assessed at 4 and 8 weeks after transfer by measuring platelet numbers (50-150 in mutant animals and >1000 in controls), spleen weight. At sacrifice (4 or 8 weeks after transfer), tibias were processed for histology and histomorphometry. Mice injected with NF-E2$^{-/-}$ spleen cells developed a phenotype indistinguishable from that of NF-E2$^{-/-}$ mice (FIG. 4). Mice sacrificed 4 weeks after injection with NF-E2$^{-/-}$ cells had an average bone volume/tissue volume (BV/TV) of 35% compared to 18% seen in mice injected with +/+ cells (approx. 2-fold increase in bone volume). Similarly, mice sacrificed at 8 weeks averaged 38% BV/TV. The bone volumes in adoptively transferred mice were similar to, and not significantly different from, the 35% bone volumes seen in 5-month-old mutant animals (the same age as animals sacrificed at 8 weeks). Overall, these adoptive transfer studies suggest that MKs increase OB number and bone formation in vivo. Finally, in recent studies by Dominici et al. [39], in mice treated with lethal total body irradiation, surviving MKs were shown to migrate to endosteal bone surfaces (in close contact with OBs) and stimulate a 2-fold increase in OB number.

Figure 5:
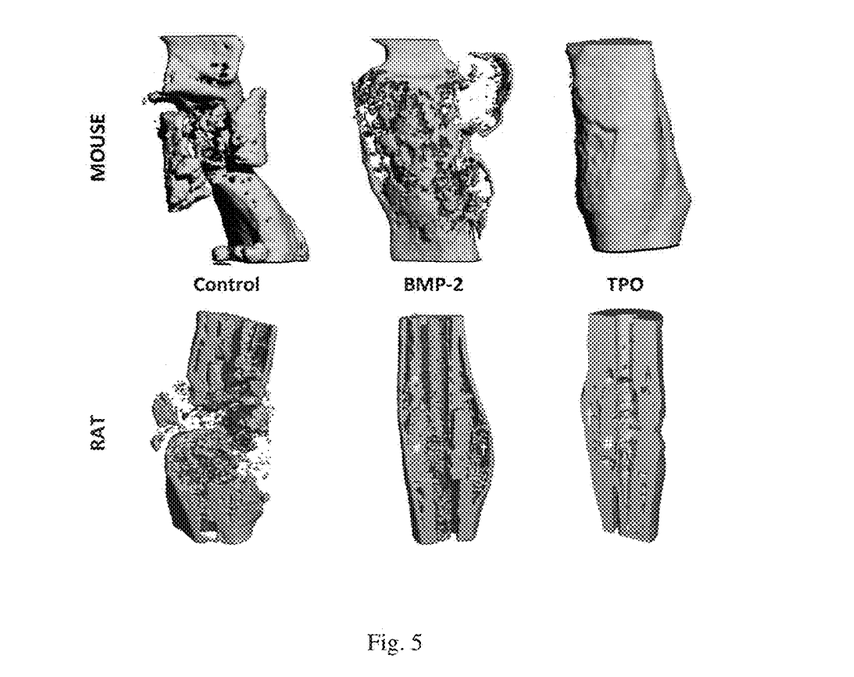
FIG. 5. µCT images of mouse and rat femurs 15 weeks post-surgery, with control (untreated) scaffolds or scaffolds containing BMP-2 (4 µg and 10 µg, respectively) or TPO (1 µg and 10 µg, respectively). # indicates the scaffold.

Referring now to FIG. 5, A pilot study (n=3) shows that TPO robustly healed a critical size defect in rat femur, more so than that observed with BMP-2. In addition, the trabeculae are thicker and the callus has undergone more remodeling than that observed with BMP-2.

While it is thought that BMP-2 works by activating osteoblasts, successful fracture repair requires remodeling and thus requires elevated osteoclast activity as well. Therefore, isolated increases in osteoblastic activity without up-regulation of osteoclastic remodeling may increase the incidence of heterotopic bone which has been reported as a complication with BMP treatment [10]. As shown in FIG. 5, it appears that at 15 weeks post-operative the TPO specimen has undergone more extensive remodeling than that observed with BMP-2. Of importance, these in vitro studies demonstrate that osteoclast progenitors express the TPO receptor and that treatment of these cells with TPO increases osteoclastogenesis by up to 5-fold (FIG. 2) [11], which may explain more extensive remodeling. A critical sized femoral defect was created in the right femur of ten-week old C57BL/6 male mice. Our scaffold was inserted into the defect site. There were 3 groups: untreated controls (n=7), TPO treated scaffolds (1 µg, n=8), and BMP-2 treated scaffolds (4 µg, n=5). X-rays of femurs 2 and 4 weeks postoperatively demonstrate bridging callus formation by 2 weeks in mice with scaffolds containing BMP-2, whereas controls remain unbridged even at 6 weeks postoperatively, confirming that the scaffold has sufficient biomechanical properties to maintain the segmental defect size. At 2 weeks, scaffolds containing TPO remain unbridged; however, at 4-6 weeks, the scaffolds containing TPO have bridged. Of importance, when comparing the 4-6 week TPO and BMP-2 scaffolds, it appears that TPO better restores the original contour of the bone which is advantageous in the clinical setting.

Figure 6:
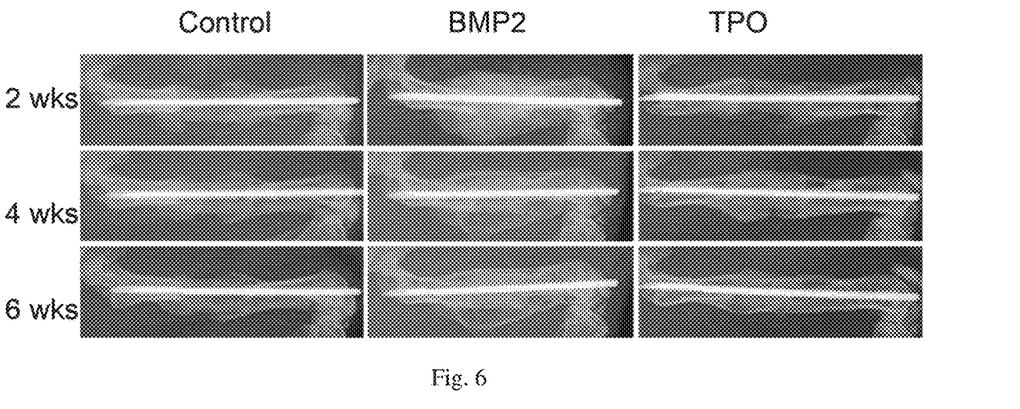
FIG. 6. X-ray images of gaps in the femurs of male mice over time having undergone three different treatments: control (left panel), BMP-2 (4 µg, middle panel), and TPO 1 µg, right panel). Images were taken 2, 4 and 6 weeks after surgery. Periosteal bridging is evident in 4 vs. 6 wks in femurs with TPO-treated scaffolds.
Figure 7A:
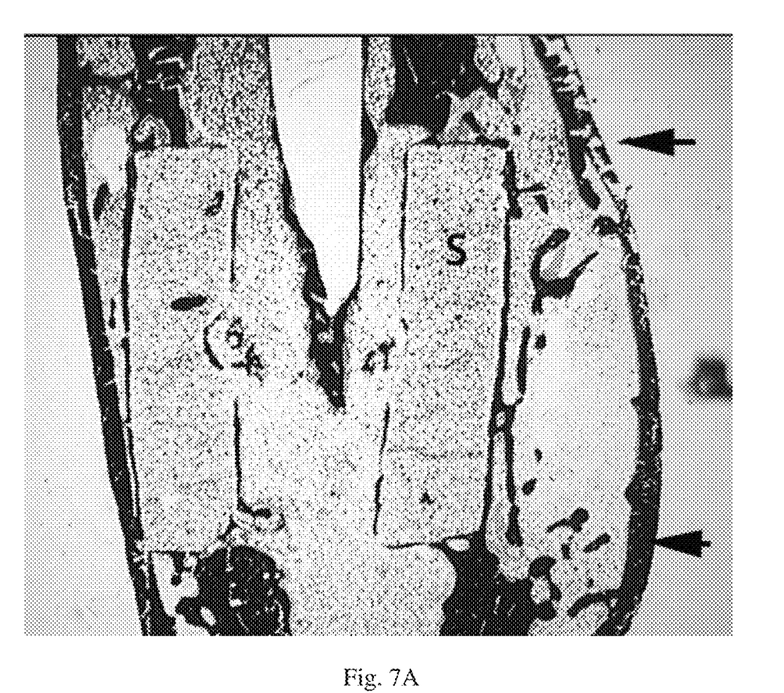
FIG. 7A. Photomicrograph of rat femur defect treated with BMP-2 (10 µg). S—denotes scaffold.
Figure 7B:
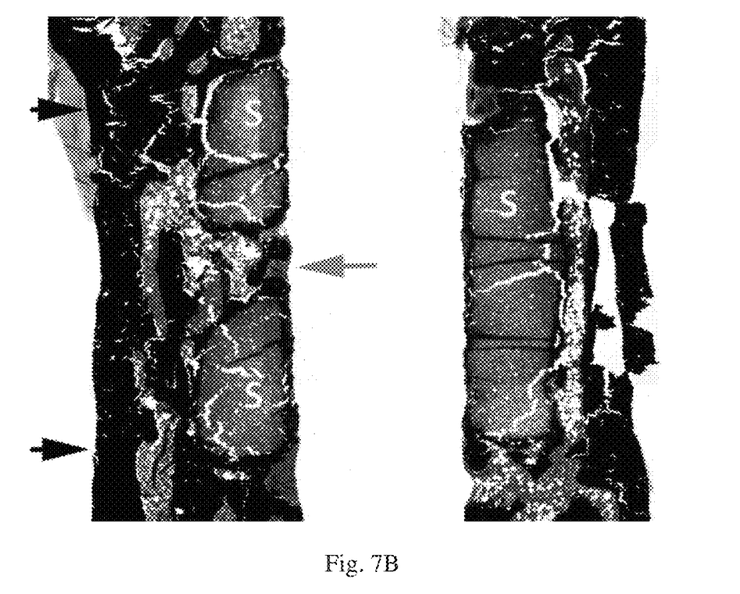
FIG. 7B. Photomicrograph of rat femur defect treated with TPO (10 µg). S—denotes scaffold.

Referring to FIG. 6, it appears that in the TPO specimens more extensive remodeling has occurred than that observed with BMP-2. While histological analyses are needed to confirm increases in osteoclastic activity, our preliminary in vitro studies demonstrate that osteoclast progenitors express the TPO receptor and that treatment of these cells with TPO increases osteoclastogenesis by up to 5-fold. It appears as though TPO offers an advantage over BMP-2 in terms of bone remodeling by increasing both osteoblasts and osteoclasts production, and it may contribute to improved/faster fracture remodeling and less heterotopic bone formation. As shown in FIG. 6, x-rays of mouse femurs taken 2, 4, and 6 week post-surgery with control (untreated) scaffolds or scaffolds that included BMP-2 (4 µg) or TPO (1 µg).

Figure 8:
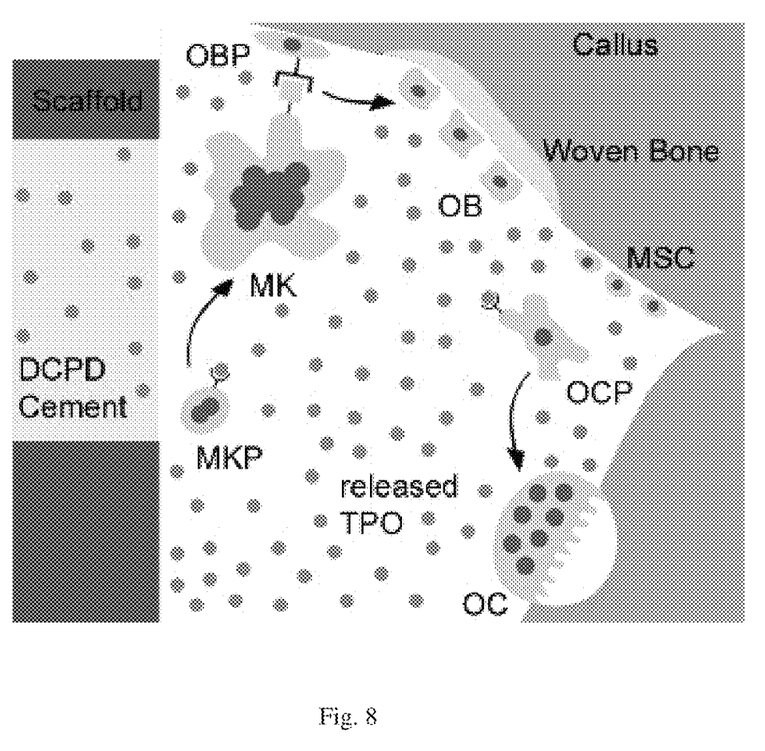
FIG. 8. Cartoon depicting a model of the scaffold and thrombopoietin in bone healing consistent with the results disclosed herein.
Figure 9:
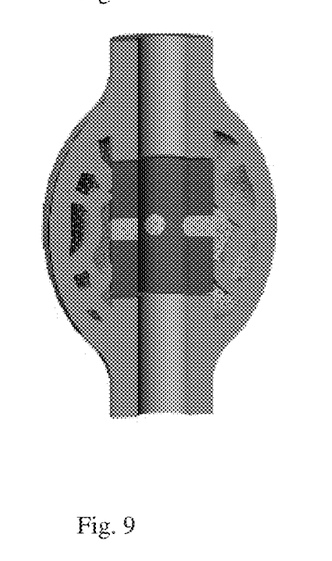
FIG. 9. Depiction of a scaffold that includes bone cement such as DCDP which can be used to deliver compounds such as TPO.
Figure 10:
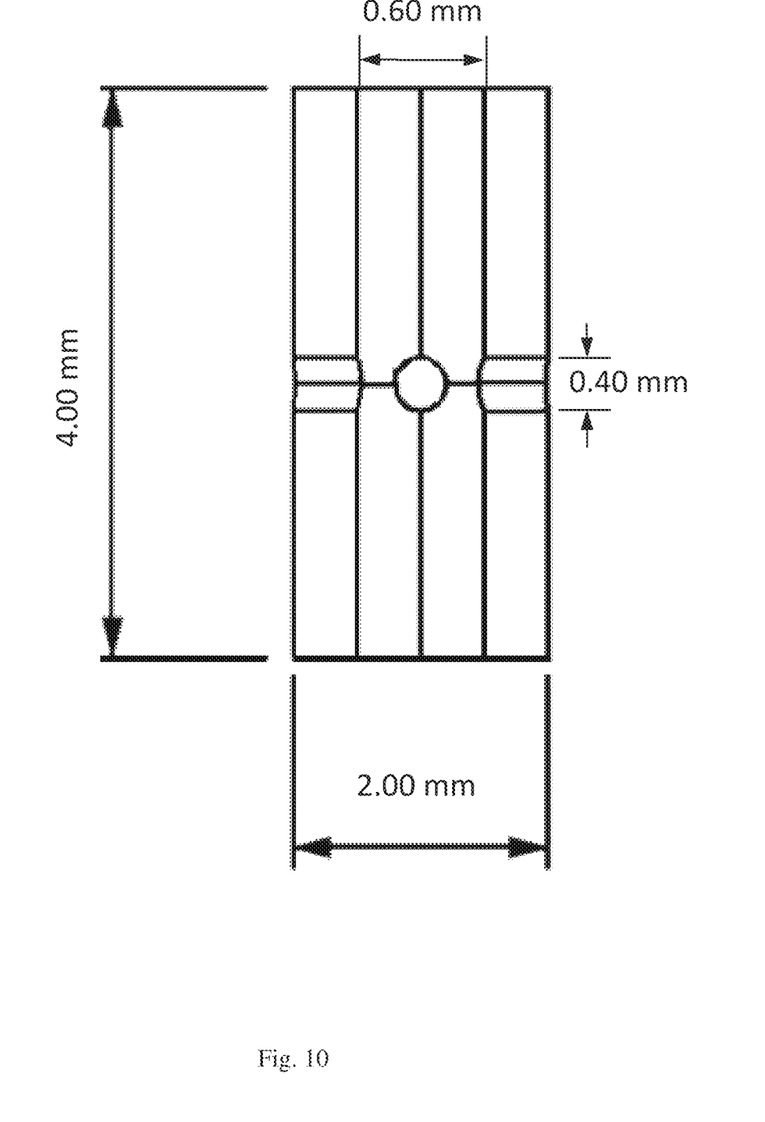
FIG. 10. Dimensions of a representative mouse femoral defect scaffold.

Referring now to FIG. 8, a simplified model of the role of TPO in bone healing. TPO released at the bone defect site binds to MKs to induce megakaryopoiesis consistent with the results present herein. Increased numbers of MKs are then available to influence OB proliferation by direct cell-to-cell contact. These OBs then form new bone. TPO at the bone defect site also binds to OC progenitors which enhances osteoclastogenesis, allowing for enhanced remodeling and less heterotopic bone formation.

TPO and megakaryocyte growth and development factor (MGDF) are thought to act by binding to the TPO receptor, c-MP1, on the surfaces of certain cells. The receptor c-MP1 belongs to the class I cytokine receptor family. Activation of the receptors in this class is thought to involve ligand-binding which induces receptor homodimerization which then initiates a cascade of signal transducing events. In addition to TPO, other compounds that have TPO like activity and presumably bind to the same receptor as TPO can be used to stimulate bone growth. Compounds with TPO like activity include those disclosed in U.S. Pat. No. 6,835,809B1 issued on Dec. 28, 2004 and U.S. Pat. No. 7,332,474 B2 issued on Feb. 19, 2008, each of which is herein incorporated by reference in its entirety as if each were incorporated individually in its entirety.

Compounds with TPO like activity include compounds that bind to and elicit a trans-membrane signal by activating the c-MP1 receptor. These compounds can be said to exhibit thrombopoietic activity.

An indirect casting approach previously described by Chu et al. *Biomaterials* 28:459-467, 2007 was used for scaffold fabrication. For additional information on related techniques, please see WO/2006-088866, which is incorporated herein by reference in its entirety. As previously reported, successful manufactured load-bearing tissue engineering scaffolds have been created and successfully used to induce bone regeneration in critical-sized segmental defects in rat femurs. Tube-shaped scaffolds were manufactured from poly(propylene) fumarate/tricalcium phosphate (PPF/TCP) composites.

A biodegradable, load-bearing carrier for delivery of material that exhibits thrombopoietic activity can be illustratively made from high strength biodegradable composites. When first implanted, the carrier provides an initial biomechanically stable environment for bone formation across the interface between bone and carrier. The osteogenic compound-carrying biodegradable carrier may provide an osteoinductive environment to attract stem cells and progenitor cells to migrate to, populate, and mineralize on the carrier surface, illustratively to form a continuous bridge between the proximal and distal segments of the bone. Finally, the degradable carrier can degrade allowing the bone to fill in the space left by carrier. The bone may then continue to remodel to physiological geometry and mechanical properties.

As used herein, the term "carrier" or "structural carrier" refers to this high strength structural carrier to be used in conjunction with an osteogenic compound such as DBM. The DBM may be supplied in a molecule carrier (i.e. hyaluronic acid, glycerol, calcium sulfate hemihydrate, etc.). When referring to such molecule carrier, the term "molecule carrier" is used. While many of the examples use DBM, it is understood that other materials that provide for an osteoinductive environment may be used as well. Such materials include, but are not limited to, bone morphogenetic protein (BMP) (including bone morphogenetic protein-2, bone morphogenetic protein-4, and bone morphogenetic protein-7), tissue growth factor beta (TGF-β), platelet-derived growth factor (PDGF), fibroblast growth factor (FGF), insulin-like growth factor (IGF), and vascular endothelial growth factor (VEGF). Moreover, the substances carried by the structural carrier are not limited to proteins. The structural carrier can include antibiotics or anti-inflammatory drugs. Suitable antibiotics include, but are not limited to, benzylpenicillin, cefazolin, clindamycin, vancomycin, nafcillin, and ciprofloxacin. The structural carrier can also include other substances to promote an osteoinductive environment including cells.

The use of DBM, BMP, or other osteogenic compounds in treating segmental defects may be combined with a high strength, load-bearing, and biodegradable carrier. When first implanted, the load-bearing carrier provides an initial biomechanically stable environment for bone formation across the bone scaffold junction. The compound having thrombopoietic activity released from the biodegradable carrier then provides an environment that stimulates bone growth and development as well as mineralization on the scaffold surface, illustratively to form a continuous bridge between the proximal and distal segments of the bone. Finally, the degradable carrier does degrade and, in time, allows the patient's own bone to fill in the space left by carrier and continue to remodel to the physiological geometry and mechanical properties.

Healing gaps larger than the critical bone gap in animals is difficult. Fortunately, the use of mechanical structures, strategically placed within the gap has helped to treat these types of bone gaps in many mammals. In some of the approaches that have worked, the mechanical structure placed in the gap is positioned so as to bear weight while allowing for bone regeneration. This achievement has rarely, if ever, been performed in the long bones of mice in the presence of growth factors alone (e.g. without the addition of cells). The exact reason for this is not known. Without being bound by any theory, hypothesis or explanation it may be that something unique to mouse physiology complicates or otherwise disfavours closing these sized gaps in mice. Still another possibility is the ratio of the defect length-to-bone length. Indeed, in the mouse a 4 mm segmental defect is required (to create a "critical sized defect" whereby the defect cannot heal on its own) and the length of mature mouse femurs is ~10-12 mm, resulting in approximately a 1:3 ratio. While in a rat, which is a much larger animal, a 5 mm segmental defect is sufficient to create a critical sized defect and as a rat femur is ~40 mm, this results in approximate 1:8 ratio of gap to overall bone length. Similarly, the cross sectional area of a rat's femur is significantly larger than the cross sectional area of a mouse's femur. The greater cross sectional area of the bone segments bracketing the critical sized defect imply that there are more margins for error when contacting a scaffold or other inset in the bone gap in a rat than there is performing a similar procedure in a mouse. Due in part to its higher gap to bone length ratio and the greater cross sectional area of the rat femur, an implant in a rat's bone gap is inherently more stable then is an implant in a corresponding gap in a mouse femur. Accordingly, it is possible that the additional stability in the rat due to the increased support on each end of the femur allows for more flexibility in the scaffold design and surgical precisions. Whereas with the reduced support and stability in the mouse femur, the precision of scaffold design, scaffold structure position, and surgical technique is of heightened importance to promote bone gap closure. Near ideally positioning of a scaffold within a bone gap requires a scaffold engineered to almost perfectly fit into the bone gap. A less than optimal alignment of the scaffold, due perhaps to imperfections in the scaffold itself and the flanking bone tissue, may result in movement of the scaffold and possible scaffold fracturing which will not allow adequate bone regeneration to close critical bone gaps in mice.

Thus, one aspect of the present invention provides an implant scaffold for facilitating bone healing in a mouse. In some embodiments, the implant includes at least one compound that exhibits thrombopoietic activity and a structural carrier formed from a biodegradable material, the structural carrier comprising a body and having at least one recess therein. In some embodiments, the scaffold may also include at least one additional material that has osteogenic activity, including, but not limited to, materials selected from the group consisting of demineralized bone matrix and bone morphogenetic protein; the body of the scaffold may form generally cylindrical shape. The scaffold body may further define a plurality of additional recesses; at least one of the additional recesses may be sized to receive a screw for plate fixation. In some embodiments, a second osteogenic material may be provided in one of the additional recesses, optionally wherein the osteogenic material and the second osteogenic material are different. In some embodiments, the compounds having thrombopoietic activity, such as TPO, may be provided in a first time release material having a first time release profile while a second osteogenic material is provided in a second time release material having a second different time release profile. In some embodiments, the second osteogenic material is VEGF and the second osteogenic material is BMP. In some embodiments, the first time release profile may have a faster time release profile than the second time release profile. In some embodiments, at least one of the recesses may include an antibiotic; the compound having thrombopoietic activity, and the osteogenic material may be absorbed into an amount of dicalcium phosphate dihydrate (DCPD) cement that has been provided in the recess, the structural carrier may possess sufficient mechanical strength to be load bearing; and the biodegradable material may be poly(caprolacton) trimethacrylate/tricalcium phosphate ("PCLTMA/TCP").

Still other aspect of the invention, an implant for facilitating bone healing in mice comprising at least one compound that exhibits thrombopoietic activity, and a structural carrier formed from a biodegradable material, the structural carrier comprising a wall extending from a first end to a second end and defining a central channel extending from an opening in the first end to an opening in the second end. In some embodiments, the longitudinal center of the scaffold or other implant is hollow and can be used to accommodate at least one rod that is parallel to the length of the implant and extends beyond the first and second distal ends of the implant in to the first and second bone fragments that bracket the critical sized gap in the bone. Within the tubular wall channel(s) or port(s) may form a generally cylindrical, elliptical, or tapered elliptical shape and the osteogenic material may be placed within at least one of the channels. In some embodiments, the body of the scaffold or other implant includes a plurality of windows extending from the exterior side wall of the implant towards the longitudinal center of implant. Optionally, the compound exhibiting thrombopoietic activity is provided in one of the windows and a second osteogenic material is provided in another of the windows. In some embodiments, at least one of the windows in the device include an antibiotic; bone growth promoting factor such as TPO may be absorbed into an amount of dicalcium phosphate dihydrate (DCPD) cement that has been provided in one of the windows. The structural carrier may possess sufficient mechanical strength to be load bearing; and the biodegradable material may be PCLTMA/TCP. In some embodiments, the osteogenic material may be selected from the group consisting of demineralized bone matrix and bone morphogenetic protein may also be added to the device.

Still other aspects of the invention include methods for repairing bone defects in mammals. Some of these methods may comprise the steps of placing a structural implant comprising a compound having thrombopoietic activity into the defect site and fixing the implant to surrounding bone tissue. Some of the methods may optionally include the step of leaving the implant in place and allowing the implant to degrade. Optionally, the fixing step may comprise using an intramedullary pin or may comprise using a plate and at least one screw.

Experimental

Materials and Methods

A pilot study utilizing the Long Evans rat femur gap model [9] which has been approved by the Laboratory Animal Care and Usage Committee (IACUC) at Indiana University was used to test a new method for repairing bone gaps. In brief, tube shape scaffolds with 4 mm external diameter, 2 mm internal diameter and 5 mm in height were manufactured from poly(propylene) fumarate/tricalcium phosphate. 10 µg of TPO or 10 µg of BMP-2 were introduced into the dicalcium phosphate dehydrate cement region of the scaffolds. In the control group, the scaffolds were left untreated (n=3/group). Segmental defects of 5 mm were created in the right femurs of male Long Evans rats. The defect was filled with a 5 mm scaffold and secured with an intramedullary K-wire placed in retrograde fashion. Femurs were imaged by x-ray to assure proper placement and integrity of the scaffold. The rats were then imaged using x-ray at three week intervals to assess continued healing. At post-operative weeks 6 and 15, rats were euthanized and femurs analyzed by x-ray, microCT, and histology.

Using microCT analysis, at post-operative week 6, none of the rat femurs showed bridging of the callus. However, at week 15, TPO robustly healed a critical sized defect in the rat femur. The cortex and trabeculae of the callus are thicker compared to the callus induced by BMP-2 in an earlier study (FIG. 5). In histological analyses, normal bone marrow was observed in the bone marrow cavity without signs of inflammatory reaction to the scaffolds at both 6 and 15 weeks. At 6 weeks, isolated bone nodules were observed in the tissues between the two bone ends, indicating the initiation of mineralization of the tissue in the gap. At 15 weeks, mineralized callus was seen bridging the two bone ends. In some areas adjacent to the scaffolds, isolated patches of cartilage with hypertrophic chondrocytes were observed, indicating the tissues were undergoing endochondral bone formation.

Referring now to FIG. 6, a critical sized femoral defect was created in the right femur of ten week old C57BL/6 male mice. A scaffold was inserted into the defect site. There were 3 groups untreated controls (n=7), TPO treated scaffolds (1 µg, n=8), and BMP-2 treated scaffolds (4 µg, n=5). X-rays of femurs 2, 4, and 6 weeks postoperatively demonstrate bridging callus formation by 2 weeks in mice with scaffolds containing BMP-2; whereas, controls remain unbridged even at 6 weeks postoperatively, confirming that the scaffold has sufficient biomechanical properties to maintain the segmental defect size. At 2 weeks, scaffolds containing TPO remain unbridged; however, at 4-6 weeks the scaffolds containing TPO have bridged. Of importance, when comparing the 4-6 week TPO and BMP-2 scaffolds, it appears that TPO better restores the original contour of the bone which is advantageous in the clinical setting.

While the novel technology has been illustrated and described in detail in the figures and foregoing description, the same is to be considered as illustrative and not restrictive in character. It being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

REFERENCES

1. Praemer A, Furrier S, Rice D P. Musculoskeletal conditions in the united states. Rosemont, Ill.: American Academy of Orthopaedic Surgeons; 1999:
2. Johnson E E, Urist M R, Finerman G A. Repair of segmental defects of the tibia with cancellous bone grafts augmented with human bone morphogenetic protein. A preliminary report. Clin Orthop Relat Res 1988; (236): 249-57.
3. M. J. Bosse, E. J. MacKenzie, in Orthopaedic Knowledge Update—Trauma 3 (American Academy of Orthopaedic Surgeons, Rosemont, Ill., 2005), pp. 65-75.
4. S. A. Goldstein, *J. Am. Acad. Orthop. Surg.* 14, S152 (2006).
5. T. Boyce, J. Edwards, N. Scarborough, *Orthop. Clin. North Am.* 30, 571 (1999).
6. S. Boraiah, O. Paul, D. Hawkes, M. Wickham, D. G. Lorich, *Clin. Orthop. Relat. Res.* 467, 3257 (2009).
7. T. J. Gao et al., *J. Biomed. Mater. Res.* 32, 505 (1996).

8. J. A. Cobos, R. W. Lindsey, Z. Gugala, *J. Orthop. Trauma* 14, 54 (2000).
9. S. Karaoglu, A. Baktir, S. Kabak, H. Arasi, *Injury* 33, 679 (2002).
10. S. Boraiah, O. Paul, D. Hawkes, M. Wickham, D. G. Lorich, *Clin. Orthop. Relat. Res.* 467, 3257 (2009).
11. J. R. Lieberman, A. Daluiski, T. A. Einhorn, *J. Bone Joint Surg. Am.* 84-A, 1032 (2002).
12. Johnson E E, Urist M R, Finerman G A. Repair of segmental defects of the tibia with cancellous bone grafts augmented with human bone morphogenetic protein. A preliminary report. Clin Orthop Relat Res 1988; (236); 249-57
13. Lane J M, Tomin E. Bostrom M P. Biosynthetic bone grafting. Clin Orthop Relat Res 1999; (367 Suppl):5107-17
14. Salkeld S L, Patron L P, Barrack R L, Cook S D. The effect of osteogenic protein-1 on the healing of segmental bone defects treated with autograft or allograft bone. J Bone Joing Surg Am 2001; 83-A:803-16
15. Watson J T, Anders M, Moed B R. Management strategies for bone loss in tibial shaft fractures. Clin Orthop Relat Res 1995; (315):138-52.
16. Weinberg H, Roth V G, Robin G C, Floman Y. Early fibular bypass procedures (tibiofibular synostosis) for massive bone loss in war injuries. J Trauma 1979; 19:177-81.
17. Green S A, Jackson J M, Wall D M, Marinow H, Ishkanian J. Management of segmental defects by the ilizarov intercalary bone transport method. Clin Orthop Relat Res 1992; (280):136-42.
18. Green S A. Skeletal defects. A comparison of bone grafting and bone transport for segmental skeletal defects. Clin Orthop Relat Res 1994; (301):111-7.
19. S. Karaoglu, A. Baktir, S. Kabak, H. Arasi, *Injury* 33, 679 (2002).
20. Kacena M A, Shivdasani R A, Wilson K, et al. Megakaryocyte-osteoblast interaction revealed in mice deficient in transcription factors GATA-1 and. NF-E2. J Bone Miner Res 2004; 19:652-60.
21. Taylor, A F, Barnes, C L T, Horowitz M C, et al. A novel role for thrombopoietin in regulating osteoclast development. JBMR. 2008; 23:SU104.
22. Kacena M A, Shivdasani R A, Wilson K., et al. Megakaryocyte-osteoblast interaction revealed in mice deficient in transcription factors GATA-1 and NF-E2, J. Bone Miner Res 2004; 19:652-60
23. M. A. Kacena et al., *J. Bone Miner. Res.* 19, 652 (2004).
24. R. A. Shivdasani et al., *Cell* 81, 695 (1995)
25. R. A. Shivdasani, Y. Fujiwara, M. A. McDevitt, S. H. Orkin, *EMBO J.* 16, 3965 (1997).
26. B. M. Frey, S. Rafii, R. G. Crystal, M. A. Moore, *Schweiz. Med. Wochenschr.* 128, 1587 (1998).
27. B. M. Frey et al., *J. Immunol.* 160, 691 (1998).
28. X. Yan et al., *Blood* 86, 4025 (1995).
29. X. Yan et al., *Blood* 88, 402 (0.1996).
30. J. L. Villeval et al., *Blood* 90, 4369 (1997).
31. L. J. Suva et al., *Am. J. Pathol.* 172, 430 (2008).
32. M. J. Perry, K. A. Redding, W. S. Alexander, J. H. Tobias, *Calcif Tissue Int.* 81, 224 (2007).
33. K. Carver-Moore et al., *Blood* 88, 803 (1996).
34. A. F. Taylor, C. L. T. Barnes, M. C. Horowitz, M. A. Kacena, "A Novel Role for Thrombopoietin in Regulating Osteoclast Development," *JBMR* 23, SU104 (2008).
35. M. A. Kacena, C. M. Gundberg, T. Nelson, M. C. Horowitz, *Bone* 36, 215 (2005).
36. M. Dominici et al., *Blood* 114, 2333 (2009).
37. M. J. Bosse, E. J. MacKenzie, in Orthopaedic Knowledge Update—Trauma 3 (American Academy of Orthopaedic Surgeons, Rosemont, Ill., 2005), pp. 65-75.
38. Chu T M, Warden S J, Turner C H, Stewart R L. Segmental bone regeneration using a load-bearing biodegradable carrier of bone morphogenetic protein-2. Biomaterials 2007; 28:459-67.

The invention claimed is:

1. A method for treating a defect site in a living bone of an animal, the method comprising applying a first exogenous compound having thrombopoietic activity to the defect site of the living bone in an amount effective to induce thrombopoiesis in the living bone, wherein the first exogenous compound activates a thrombopoietin receptor, thereby accelerating bone formation at the defect site.

2. The method of claim 1, wherein the first exogenous compound is romiplostim or megakaryocyte growth and development factor (MGDF).

3. The method of claim 1, wherein the defect is a segmental bone defect.

4. The method of claim 3, wherein the segmental bone defect is a critical sized defect.

5. The method of claim 3, wherein the segmental bone defect is a nonunion.

6. The method of claim 3, wherein the accelerated bone formation is characterized by increased osteoblast production and osteoclastogenesis within the segmental bone defect.

7. The method of claim 1, wherein the first exogenous compound is contained in a formulation selected from the group consisting of a paste, a glue, a coating, a gel, a powder, and a liquid.

8. The method of claim 1, further comprising applying to the defect site a second exogenous compound that stimulates bone growth, wherein the second exogenous compound is distinct from the first exogenous compound.

9. The method of claim 8, wherein the second exogenous compound is bone morphogenetic protein 2 (BMP-2).

10. The method of claim 2, wherein the defect is a segmental bone defect.

11. The method of claim 10, wherein the segmental bone defect is a critical sized defect.

12. The method of claim 10, wherein the segmental bone defect is a nonunion.

13. The method of claim 10, wherein the accelerated bone formation is characterized by increased osteoblast production and osteoclastogenesis within the segmental bone defect.

14. The method of claim 2, wherein the first exogenous compound is contained in a formulation selected from the group consisting of a paste, a glue, a coating, a gel, a powder, and a liquid.

15. The method of claim 2, further comprising applying to the defect site a second exogenous compound that stimulates bone growth, wherein the second exogenous compound is distinct from the first exogenous compound.

16. The method of claim 15, wherein the second exogenous compound is BMP-2.

17. A method for repairing a segmental bone defect in an animal bone, the method comprising providing a biodegradable bone repair scaffold that contains a first compound having thrombopoietic activity and inserting the scaffold into the segmental bone defect, wherein the first compound activates a thrombopoietin receptor, thereby accelerating bone formation such that bridging occurs at the segmental bone defect sufficient to repair the defect.

18. The method of claim 17, wherein the first compound is romiplostim or MGDF.

19. The method of claim 17, wherein the scaffold further contains a second compound that stimulates bone growth, wherein the second compound is distinct from the first compound.

20. The method of claim 19, wherein the second compound is BMP-2.

21. The method of claim 17, wherein the accelerated bone formation is characterized by increased osteoblast production and osteoclastogenesis within the segmental bone defect.

22. The method of claim 18, wherein the accelerated bone formation is characterized by increased osteoblast production and osteoclastogenesis within the segmental bone defect.

23. A method for treating a defect site in a living bone of an animal, the method comprising administering a compound having thrombopoietic activity to the animal having a defect site in the living bone in an amount effective to induce thrombopoiesis in the living bone, wherein the compound induces accelerated bone formation at the defect site.

24. The method of claim 23, wherein the compound is administered by injection.

25. The method of claim 23, wherein the compound is thrombopoietin, romiplostim, or megakaryocyte growth and development factor.

* * * * *